US006113929A

United States Patent [19]

Karl

[11] Patent Number: 6,113,929

[45] Date of Patent: Sep. 5, 2000

[54] COMPOSITION OF MATTER AND METHOD FOR REMOVING PLANT RESINS FROM SKIN

[76] Inventor: A. Robert Karl, 940 Washburn La., Medford, Oreg. 97501

[21] Appl. No.: 09/128,367

[22] Filed: Aug. 3, 1998

[51] Int. Cl.[7] ....... A61K 7/02

[52] U.S. Cl. ....... 424/401; 424/400; 424/78.06; 424/78.05; 514/862; 514/886; 514/887

[58] Field of Search ....... 424/400, 401, 424/405, 406, 78.05, 78.06; 514/827, 862, 886, 887, 782

[56] References Cited

U.S. PATENT DOCUMENTS

| | | | |
|---|---|---|---|
| 4,447,418 | 5/1984 | Maddoux | 424/165 |
| 4,879,116 | 11/1989 | Fox et al. | 424/682 |
| 4,895,727 | 1/1990 | Allen | 424/642 |
| 5,443,847 | 8/1995 | West | 424/639 |
| 5,888,515 | 3/1999 | Albert et al. | 424/195.1 |

*Primary Examiner*—Thurman K. Page
*Assistant Examiner*—Lakshmi Channavajjala
*Attorney, Agent, or Firm*—Daniel J. Bedell; Smith-Hill and Bedell

[57] ABSTRACT

Plant resin exuded by poison ivy, poison oak, poison sumac and other plant resins are removed from the skin by successive applications of an alkaline cleanser and acidic stripper. The skin is first thoroughly washed with the alkaline cleanser. After rinsing the cleanser from the skin, the skin is daubed with the acidic stripper. The alkaline cleanser is a mixture of water, soap, turpentine, a mild abrasive, and mineral spirits. The acidic stripper is a mixture of an acid, and astringents such as tannin and witch hazel extract.

16 Claims, No Drawings

COMPOSITION OF MATTER AND METHOD FOR REMOVING PLANT RESINS FROM SKIN

BACKGROUND OF THE INVENTION

1. Field of the Invention

The present invention relates in general to treatments for preventing or reducing contact dermatitis caused by plant resins, and in particular to the use of cleansers and strippers for removing plant resins from the skin.

2. Description of Related Art

Poison oak, poison ivy, poison sumac, poison wood and approximately 150 other plant species are members of the genus Rhus, a shrub or small tree growing in tropical and temperate areas of the Americas, Europe and Asia. Many of these plants exude a sticky, resinous sap containing urushiol, a powerful irritant which can cause a severe skin rash. The resinous saps of other types of plants can also irritate the skin. The severity of the irritation can be greatly reduced when the resin is quickly and thoroughly removed from the skin. However plant resins stick to the skin and are not readily dissolved or removed.

Various methods for removing plant resin from the skin have been suggested. The most commonly suggested method is to wash the affected area with soap. Since some soaps contain oils that spread the resin to other areas of the skin, brown laundry soap made from saponified fats which do not contain the oils found in most bath soaps is preferred. Some people have suggested the use of dilute acids such as oxalic acid (contained in rhubarb), tannic acid (oak bark), and acetic acid (vinegar) to dissolve the plant resin. However while helpful, neither soap nor dilute acids completely remove the resin from the skin because plant resin, being a complex substance, is not completely dissolved by either type of wash.

What is needed is a system for effectively removing substantially all plant resin from affected areas the skin.

SUMMARY OF THE INVENTION

In accordance with one aspect of the invention, plant resin is removed from the skin by first scrubbing the skin with an alkaline cleanser that is a mixture of water, soap, turpentine, mineral spirits and oatmeal. The soap helps to loosen the dead outer layer of skin cells and the water in the soap dissolves some components of the resin. Turpentine, a solvent made from resinous wood sap, and the mineral spirits help to dissolve other components of the resin. The oatmeal acts as a gentle scouring agent for removing skin and breaking up the resin to improve the effectiveness of the soap, water and turpentine.

In accordance with another aspect of the invention, the alkaline cleanser is rinsed away and the affected area of the skin is then daubed with an acidic stripper, suitably a mixture of water, an acid (e.g. acetic or oxalic acid), tannin, and witch hazel extract. The acid helps to dissolve any remaining resin. Astringents tannin and witch hazel extract cause the skin pores to close, to prevent any residual resin from working its way into the pores.

The combination of the alkaline cleanser and the acidic stripper applied successively will remove substantially all of the plant resin from the skin and is particularly effective in reducing the severity and duration of the rash even when employed after onset of the rash.

It is accordingly an object of the invention to provide a system for effectively removing plant resin from the skin.

The concluding portion of this specification particularly points out and distinctly claims the subject matter of the present invention. However those skilled in the art will best understand both the organization and method of operation of the invention, together with further advantages and objects thereof, by reading the remaining portions of the specification.

DESCRIPTION OF THE PREFERRED EMBODIMENT(S)

Poison oak, poison ivy, poison sumac, poison wood and approximately 150 other plant species are members of the genus Rhus, a shrub or small tree growing in tropical and temperate areas of the Americas, Europe and Asia. Many of these plants exude a resinous sap containing urushiol, a powerful irritant which can cause a severe skin rash.

In accordance with the present invention a two-step process is used for removing substantially all of such plant resins from affected areas the skin. In the first step, the affected area of skin is scrubbed with an alkaline cleanser that is a mixture of water, soap, turpentine and oatmeal suitably in accordance with the following Table I:

TABLE I

| INGREDIENT | AMOUNT (by volume) |
|---|---|
| water | 60.0 to 93.0% |
| soap solids | 6.0% to 40.0% |
| oatmeal | 1.0% to 10.0% |
| turpentine | 0.1% to 5.0% |
| mineral spirits | 0.05% to 4.0% |

The soap, suitably made from saponified fats not containing bath soap oils, loosens the dead outer layer of skin cells and, along with the water, dissolves some components of the resin. The turpentine, a solvent made from resinous wood sap, and the mineral spirits help to dissolve other components of the resin. The oatmeal acts as a gentle scouring agent for removing skin and breaking up the resin to improve the effectiveness of the soap, water and turpentine. The oatmeal also has a soothing effect on the skin.

In the second step of the process, the affected area is daubed with an acidic stripper, a mixture of acetic acid, tannin, and witch hazel extract (double distilled) suitably in the proportions indicated in the following Table II:

TABLE II

| INGREDIENT | AMOUNT (by volume) |
|---|---|
| acetic acid (3–10% solution) | 51.0% to 99.5% |
| witch hazel extract | 0.1% to 5% |
| tannin solution | 0.1% to 48/9% |

In preparing the stripper, a sufficient amount tannin solution (suitably in the form of strong tea) is added to the acetic acid to bring the pH of the solution to a range of 2.2 to 4.5. The witch hazel extract is then added to the mixture. The acetic acid helps to dissolve any remaining resin. The tannin and witch hazel extract are astringents which cause the skin pores to close to prevent any residual resin from working its way into the pores.

Since the alkaline cleanser and the acidic stripper react with one another they should not be mixed. The cleanser should therefore be thoroughly rinsed from the skin before the stripper is applied. The use of the cleanser alone or the acidic stripper alone will in some cases be sufficient to remove plant resin from the skin. However use of both the alkaline cleanser and the acidic stripper is normally more effective in removing plant resins from the skin and is particularly effective in reducing the severity and duration of the rash even when employed after onset of the rash. The order in which the stripper and the cleanser are applied to the skin may be reversed. However the process is normally more effective when the cleanser is applied before the stripper.

While the forgoing specification has described a preferred embodiment of the present invention, one skilled in the art may make many modifications to the preferred embodiment without departing from the invention in its broader aspects. In particular various substitutions can be made for cleanser and stripper ingredients and, while the effectiveness of the treatment will be reduced, some ingredients may be omitted. For example the abrasive oatmeal and/or mineral spirits may be omitted from the cleanser. Other mild abrasives, such as for example pumice, may be substituted for the oatmeal in the cleanser. In the stripper, other acids such as oxalic acid or tannic acid may be substituted for the acidic acid and the tannin and/or witch hazel extract can be replaced by other astringents. Astringents may be omitted from the stripper. Turpentine and/or an abrasive such as oatmeal or pumice may also be added to the stripper. The appended claims therefore are intended to cover all such modifications as fall within the true scope and spirit of the invention.

I claim:

1. A method for removing plant resin from skin comprising the steps of;

washing the skin with an alkaline cleanser, removing the alkaline cleanser from the skin, applying an acidic stripper to the skin, and removing the acidic stripper from the skin, wherein said alkaline cleanser comprises soap and water, and wherein said acidic stripper has a pH of 2.7–4.5.

2. The method in accordance with claim 1 wherein said alkaline cleanser further comprises turpentine.

3. The method in accordance with claim 2 wherein said alkaline cleanser further comprises mineral spirits.

4. The method in accordance with claim 1 wherein said acidic stripper comprises an astringent.

5. The method in accordance with claim 4 wherein said alkaline cleanser further comprises turpentine.

6. The method in accordance with claim 4 wherein said astringent comprises tannin.

7. The method in accordance with claim 4 wherein said astringent comprises witch hazel extract.

8. The method in accordance with claim 4 wherein said astringent comprises tannin and witch hazel extract.

9. The method in accordance with claim 2 wherein said alkaline cleanser further comprises an abrasive.

10. The method in accordance with claim 9 wherein said abrasive comprises oatmeal.

11. The method in accordance with claim 1 wherein said alkaline cleanser comprises by volume:

60.0 to 93.0% water 6.0% to 40.0% soap 1.0% to 10.0% oatmeal, and 0.1% to 5.0% turpentine.

12. The method in accordance with claim 11 wherein said acid stripper comprises tannin, acid and witch hazel extract.

13. The method in accordance with claim 12 wherein said alkaline cleanser further comprises mineral spirits.

14. A method for removing plant resin from skin comprising the steps of:

washing the skin and applying an acidic stripper to the skin, wherein said acidic stripper comprises water, an acid, and an astringent.

15. The method in accordance with claim 14 wherein said astringent comprises at least one of tannin and witch hazel extract.

16. The method in accordance with claim 14 wherein said acid stripper has a pH of 2.7–4.5 and comprises an acid, witch hazel extract, and tannin.

* * * * *